US010729310B2

(12) United States Patent
Takahashi

(10) Patent No.: US 10,729,310 B2
(45) Date of Patent: Aug. 4, 2020

(54) ENDOSCOPE IMAGE PROCESSING DEVICES

(71) Applicant: OLYMPUS CORPORATION, Tokyo (JP)

(72) Inventor: Hiromi Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/418,249

(22) Filed: May 21, 2019

(65) Prior Publication Data

US 2019/0269299 A1 Sep. 5, 2019

Related U.S. Application Data

(63) Continuation of application No. PCT/JP2016/085898, filed on Dec. 2, 2016.

(51) Int. Cl.
*A61B 1/00* (2006.01)
*G16H 30/40* (2018.01)
(Continued)

(52) U.S. Cl.
CPC ............ *A61B 1/00009* (2013.01); *A61B 1/04* (2013.01); *A61B 1/0676* (2013.01);
(Continued)

(58) Field of Classification Search
CPC ........ G16H 30/40; G16H 40/63; G16H 30/20; G06T 7/0012; G02B 23/24;
(Continued)

(56) References Cited

U.S. PATENT DOCUMENTS

2003/0078477 A1 4/2003 Kang et al.
2003/0169354 A1 9/2003 Aotsuka
(Continued)

FOREIGN PATENT DOCUMENTS

EP 3207855 A1 8/2017
JP H04-341232 A 11/1992
(Continued)

OTHER PUBLICATIONS

Office Action dated Feb. 12, 2020 received in U.S. Appl. No. 15/701,653.
(Continued)

*Primary Examiner* — Tung T Vo
(74) *Attorney, Agent, or Firm* — Scully, Scott, Murphy & Presser, P.C.

(57) ABSTRACT

An endoscope image processing device includes a processor including hardware programmed to: enlarge or reduce multiple color component images constituting a normal light image, and a narrow-band light image; generate a blended image by synthesizing one of the enlarged or reduced color component images and the enlarged or reduced narrow-band light image; and generate a color superimposed image by synthesizing the blended image and the other enlarged or reduced color component images. The processor is programmed to replace some of pixels of the one color component image with corresponding pixels of the narrow-band light image such that distribution of pixels of the one color component image and pixels of the narrow-band light image is substantially uniform over the blended image.

13 Claims, 12 Drawing Sheets

(51) Int. Cl.
*A61B 1/04* (2006.01)
*A61B 1/06* (2006.01)
*G06T 7/00* (2017.01)
*G02B 23/24* (2006.01)

(52) U.S. Cl.
CPC ........... *G06T 7/0012* (2013.01); *G16H 30/40* (2018.01); *G02B 23/24* (2013.01)

(58) Field of Classification Search
CPC ................ G02B 27/1006; G02B 23/26; G02B 23/2484; A61B 1/00009; A61B 1/04; A61B 1/0676; A61B 1/0638
USPC .......................................................... 348/65
See application file for complete search history.

(56) References Cited

U.S. PATENT DOCUMENTS

| | | |
|---|---|---|
| 2004/0155957 A1 | 8/2004 | Kobayashi |
| 2006/0247535 A1 | 11/2006 | Sendai |
| 2008/0088857 A1 | 4/2008 | Zimmer et al. |
| 2008/0170137 A1 | 7/2008 | Matsumoto et al. |
| 2010/0245616 A1 | 9/2010 | Yoshino et al. |
| 2010/0289885 A1 | 11/2010 | Lu et al. |
| 2011/0009702 A1 | 1/2011 | Morishita et al. |
| 2011/0109761 A1 | 5/2011 | Shimotsu et al. |
| 2012/0328175 A1 | 12/2012 | Watanabe |
| 2013/0077862 A1 | 3/2013 | Nomura et al. |
| 2013/0193311 A1 | 8/2013 | Yoshida |
| 2013/0208101 A1 | 8/2013 | Ono |
| 2015/0018690 A1 | 1/2015 | Kang et al. |
| 2015/0042774 A1 | 2/2015 | Sugano et al. |
| 2015/0092032 A1 | 4/2015 | Kuramoto |
| 2015/0104090 A1* | 4/2015 | Hopfgartner ........... G06T 17/10 382/131 |
| 2016/0351609 A1 | 12/2016 | Borthakur |
| 2017/0061230 A1 | 3/2017 | Sato |
| 2017/0180641 A1 | 6/2017 | Yamada |
| 2017/0280029 A1 | 9/2017 | Steiner |
| 2018/0000317 A1 | 1/2018 | Mitamura |
| 2018/0000401 A1 | 1/2018 | Kang et al. |

FOREIGN PATENT DOCUMENTS

| | | |
|---|---|---|
| JP | 2004-236952 A | 8/2004 |
| JP | 2004-321244 A | 11/2004 |
| JP | 2007-089840 A | 4/2007 |
| JP | 2011-101771 A | 5/2011 |
| JP | 2011-194164 A | 10/2011 |
| JP | 4799109 B2 | 10/2011 |
| JP | 2012-010962 A | 1/2012 |
| JP | 2015-029841 A | 2/2015 |
| WO | WO 2016/059977 A1 | 4/2016 |
| WO | WO 2016/147366 A1 | 9/2016 |

OTHER PUBLICATIONS

Office Action dated Sep. 10, 2019 received in U.S. Appl. No. 15/701,653.
International Search Report dated Feb. 21, 2017 issued in PCT/JP2016/085898.
International Search Report dated May 19, 2015 issued in PCT/JP2015/058169.

* cited by examiner

FIG. 11A

| G11 | G12 | G13 | G14 | G15 |
| --- | --- | --- | --- | --- |
| G21 | G22 | G23 | G24 | G25 |
| G31 | G32 | G33 | G34 | G35 |
| G41 | G42 | G43 | G44 | G45 |
| G51 | G52 | G53 | G54 | G55 |

FIG. 11B

| G11 |  | G12 |  | G13 |
| --- | --- | --- | --- | --- |
|  |  |  |  |  |
| G21 |  | G22 |  | G23 |
|  |  |  |  |  |
| G31 |  | G32 |  | G33 |

FIG. 11C

| G11 |  | G12 |  | G13 |
| --- | --- | --- | --- | --- |
|  | G22' |  | G24' |  |
| G21 |  | G22 |  | G23 |
|  | G42' |  | G44' |  |
| G31 |  | G32 |  | G33 |

FIG. 12A

| F11 | F12 | F13 | F14 | G15 |
|-----|-----|-----|-----|-----|
| F21 | F22 | F23 | F24 | F25 |
| F31 | F32 | F33 | F34 | F35 |
| F41 | F42 | F43 | F44 | F45 |
| F51 | F52 | F53 | F54 | F55 |

FIG. 12B

| F11 |  | F12 |  | F13 |
|-----|--|-----|--|-----|
|     |  |     |  |     |
| F21 |  | F22 |  | F23 |
|     |  |     |  |     |

FIG. 12C

|     | F02' |     | F04' |     |
|-----|------|-----|------|-----|
| F11 | F12  |     | F13  |     |
|     | F31' |     | F34' |     |
| F21 | F22  |     | F23  |     |
|     | F52' |     | F54' |     |

ENDOSCOPE IMAGE PROCESSING DEVICES

CROSS-REFERENCE TO RELATED APPLICATIONS

This is a continuation of International Application PCT/JP2016/085898 which is hereby incorporated by reference herein in its entirety.

TECHNICAL FIELD

The present invention relates to an endoscope image processing device.

BACKGROUND ART

An endoscope device has been conventionally known which acquires a normal light image such as a white light image and a narrow-band light image such as a fluorescence image, and superimposedly displays the normal light image and the narrow-band light image (for example, see PTL 1). In a method for superimposing the normal light image and the narrow-band light image in PTL 1, the narrow-band light image is added to one of three-color component images of R, G, B constituting the normal light image.

CITATION LIST

Patent Literature

{PTL 1}
the Publication of Japanese Patent No. 4799109

SUMMARY OF INVENTION

One aspect of the present invention is an endoscope image processing device processing a color normal light image of a subject illuminated with wide-band visible light and a narrow-band light image of the subject illuminated with a narrow-band light, the image processing device including: a processor comprising hardware programmed to: enlarge or reduce multiple color component images constituting the normal light image, and the narrow-band light image; generate a blended image by synthesizing one of the enlarged or reduced color component images and the enlarged or reduced narrow-band light image; and generate a color superimposed image by synthesizing the blended image and the other enlarged or reduced color component images, wherein the processor is programmed to generate the blended image by selecting some of pixels of the one enlarged or reduced color component image, and replacing the selected pixels with corresponding pixels of the enlarged or reduced narrow-band light image, and replace some of pixels of the one enlarged or reduced color component image with pixels of the enlarged or reduced narrow-band light image such that distribution of pixels of the one enlarged or reduced color component image and pixels of the enlarged or reduced narrow-band light image is substantially uniform over the blended image.

BRIEF DESCRIPTION OF DRAWINGS

FIG. 11A is a diagram showing a G component image generated by an enlargement/reduction unit.

FIG. 11B is an explanatory diagram of a process of adding blank pixels to the G component image in FIG. 11A.

FIG. 11C is an explanatory diagram of a process of interpolating the blank pixels in the G component image in FIG. 11B.

FIG. 12A is a diagram showing a fluorescence image generated by the enlargement/reduction unit.

FIG. 12B is an explanatory diagram of a process of adding blank pixels to the fluorescence image in FIG. 12A.

FIG. 12C is an explanatory diagram of a process of interpolating the blank pixels in the fluorescence image in FIG. 12B.

DESCRIPTION OF EMBODIMENTS

First Embodiment

An endoscope image processing device 1 according to a first embodiment of the present invention and an endoscope system 100 provided therewith will be described with reference to FIGS. 1 to 5.

Figure 1:
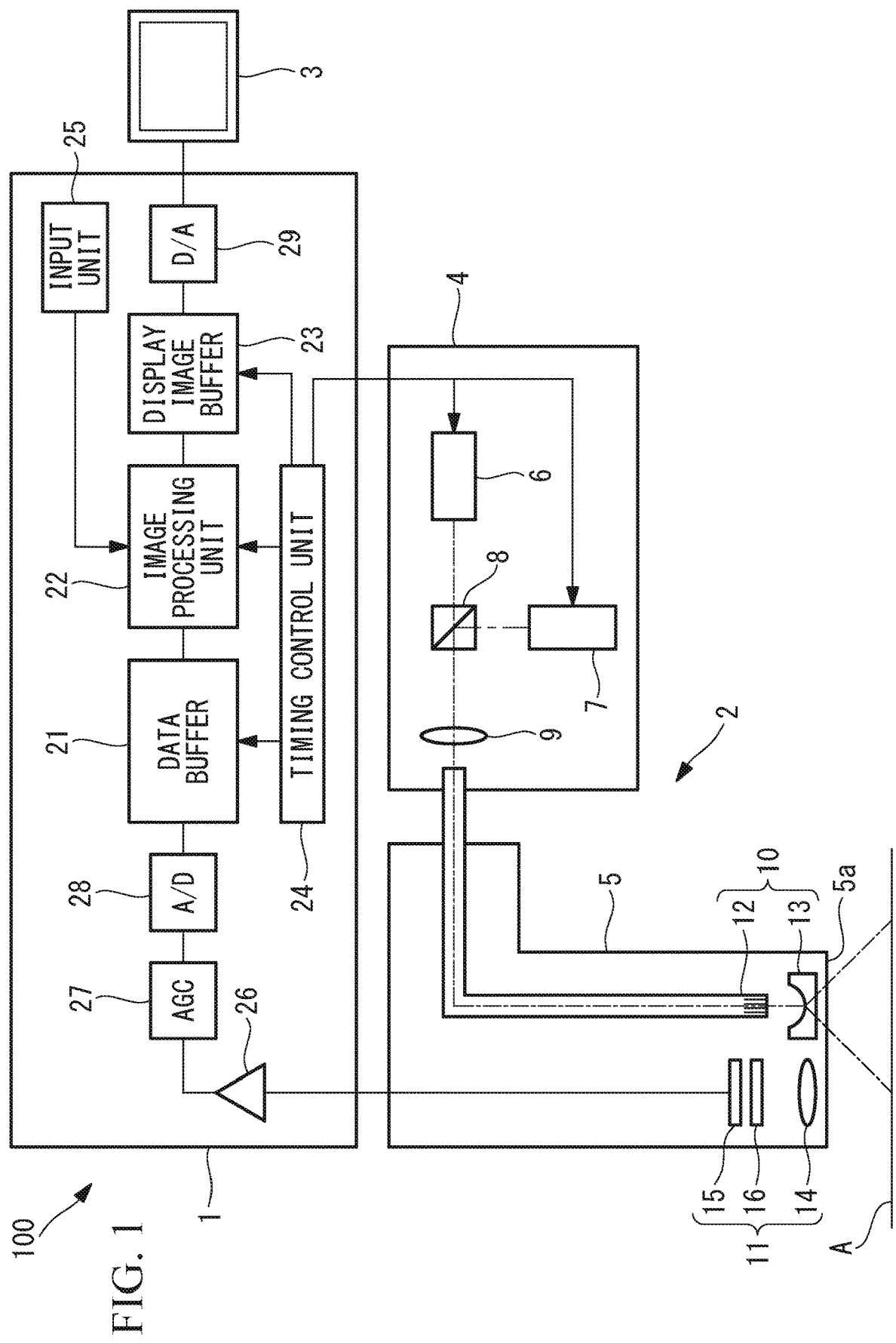
FIG. 1 is an entire configuration diagram of an endoscope image processing device and an endoscope system according to a first embodiment of the present invention.

As illustrated in FIG. 1, the endoscope system 100 includes an endoscope device 2 that acquires a white light image signal and a fluorescence image signal of a biotissue (subject) A, the endoscope image processing device (hereinafter, simply referred to as "image processing device") 1 connected with the endoscope device 2, and a display device 3 connected with the image processing device 1.

The endoscope device 2 includes a light source unit 4 which outputs white light and excitation light, and an insertion part 5 which can be inserted into a human body and which acquires an image signal by irradiating the biotissue A in the human body with the white light and excitation light from the light source unit 4.

The light source unit 4 includes a white light source 6 which emits white light, an excitation light source 7 which emits excitation light, a beam splitter 8 through which the white light from the white light source 6 and the excitation light from the excitation light source 7 exit, and a lens 9 onto which the white light and excitation light having exited from the beam splitter 8 are converged.

For example, the white light source 6 is a semiconductor light source such as an LED, or a lamp light source such as an Xe lamp. For example, the excitation light source 7 is a semiconductor light source such as a laser diode. The beam splitter 8 allows white light to transmit therethrough, reflects excitation light (e.g., infrared light) the wavelength of which is longer than that of the white light, and thereby, synthesizes the white light and the excitation light on the same optical axis. The white light source 6 and the excitation light source 7 are controlled by a timing control unit 24 (described later) so as to be alternately lit. Therefore, the white light and the excitation light are alternately outputted from the light source unit 4. The white light and the excitation light may be simultaneously outputted after being synthesized.

The insertion part 5 includes a lighting unit 10 which applies the white light and excitation light supplied from the light source unit 4 toward the biotissue A through a distal end 5a of the insertion part 5, and an image pickup unit 11 which is provided to the distal end 5a of the insertion part 5 and which photographs the biotissue A.

The lighting unit 10 includes a light guide fiber 12 which is disposed over substantially the whole length, in the longitudinal direction, of the insertion part 5, and a lighting optical system 13 which is provided to the distal end 5a of the insertion part 5. The light guide fiber 12 guides, from the proximal end to the distal end thereof, the light converged onto the lens 9. The lighting optical system 13 diffuses the white light and the excitation light having exited from the distal end of the light guide fiber 12, and applies the white light and the excitation light to the biotissue A facing the distal end 5a of the insertion part 5.

The image pickup unit 11 includes an objective lens 14 which collects light from the biotissue A, a color image pickup element 15 which is disposed on an image forming plane of the objective lens 14 and which photographs the light collected by the objective lens 14, and a notch filter 16 which is disposed between the objective lens 14 and the image pickup element 15 and which selectively cuts the excitation light.

The image pickup element 15 is a CCD image sensor or a CMOS image sensor having an RGB mosaic filter. The image pickup element 15 receives white light or fluorescence having passed through the notch filter 16, generates an image signal by photoelectronic conversion of the received light, and transmits the generated image signal to the image processing device 1.

The image processing device 1 includes a data buffer 21 which temporarily holds the image signal received from the image pickup element 15, an image processing unit 22 that processes the image signal received from the data buffer 21, and thereby, generates a superimposed image in which a white light image (normal light image) and a fluorescence image (narrow-band light image) are superimposed, a display image buffer 23 which temporarily holds the superimposed image outputted from the image processing unit 22, the timing control unit 24 that synchronizes the operations of the light source unit 4, the image pickup element 15, the buffers 21, 23, and the image processing unit 22, and an input unit 25.

Reference numeral 26 denotes an amplifier that amplifies the image signal outputted from the image pickup element 15. Reference numeral 27 denotes a gain controller (AGC). Reference numeral 28 denotes an A/D converter that converts an analog image signal to a digital image signal. Reference numeral 29 denotes a D/A converter that converts a digital image signal of a superimposed image outputted from the display image buffer 23 to an analog image signal.

The timing control unit 24 causes the white light source 6 and the excitation light source 7 to light up alternately, and causes the image pickup element 15 to perform exposure in synchronization with the white light source 6 and the excitation light source 7. Consequently, the image pickup element 15 alternately obtains a white light image signal based on the white light reflected by the biotissue A and a fluorescence image signal based on fluorescence generated at the biotissue A, and transmits the signals to the image processing device 1.

The display device 3 has, on a screen thereof, a display area for displaying a superimposed image. The input unit 25 is configured to allow an observer to input thereinto a display magnification for the superimposed image which is displayed in the display area of the display device 3. Here, a display magnification indicating enlargement of the superimposed image is referred to as "enlargement rate", and a display magnification indicating reduction of the superimposed image is referred to as "reduction rate". For example, when the display magnification representing the rate of unmagnification is 100%, a display magnification higher than 100% is referred to as "enlargement rate", and a display magnification lower than 100% is referred to as "reduction rate".

The data buffer 21 temporarily holds image signals received from the image pickup element 15, and transmits one pair of a white light image signal and a fluorescence image signal to the image processing unit 22.

Figure 2:
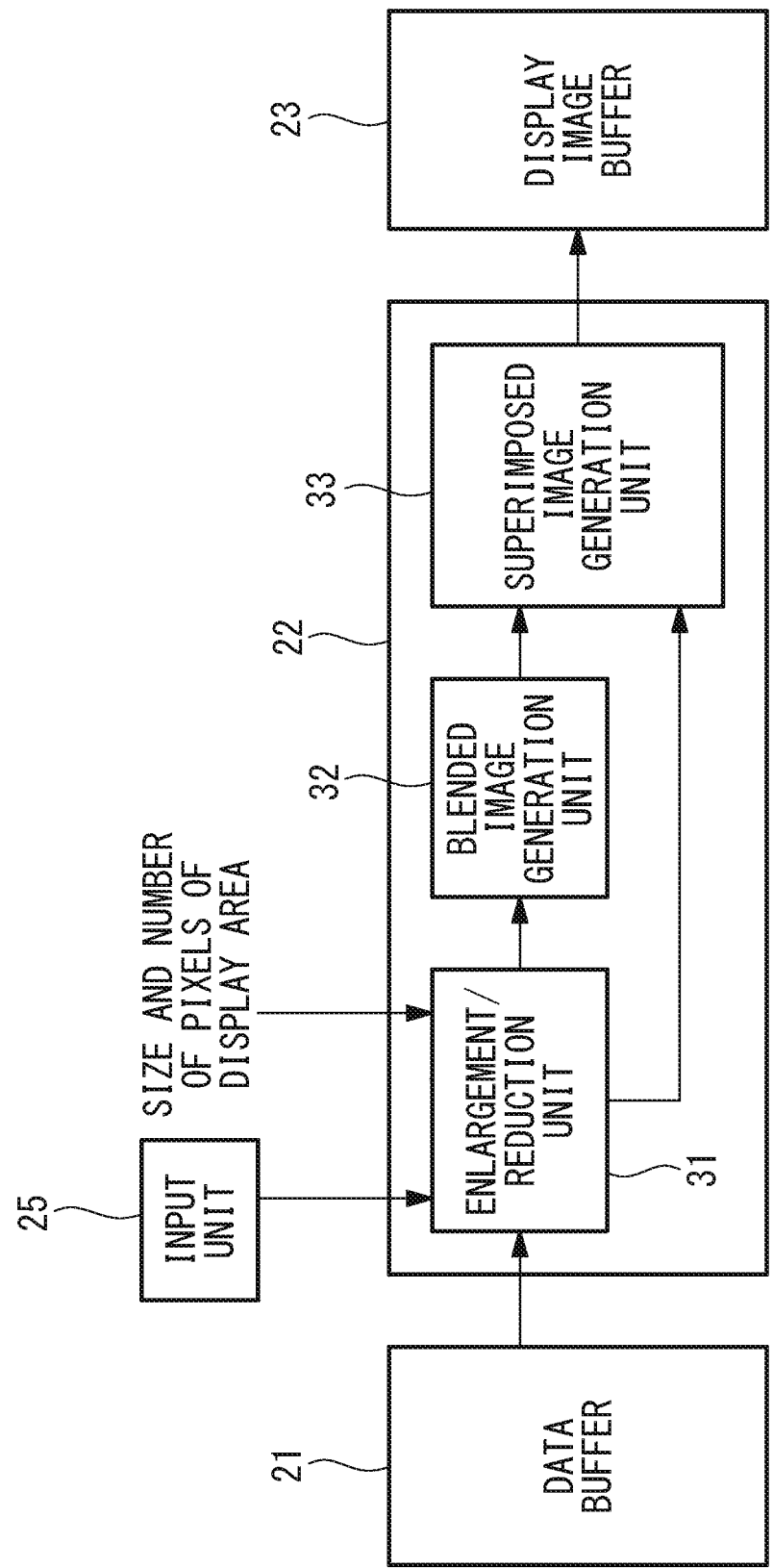
FIG. 2 is a configuration diagram of an image processing unit of the endoscope image processing device in FIG. 1.
Figure 3:
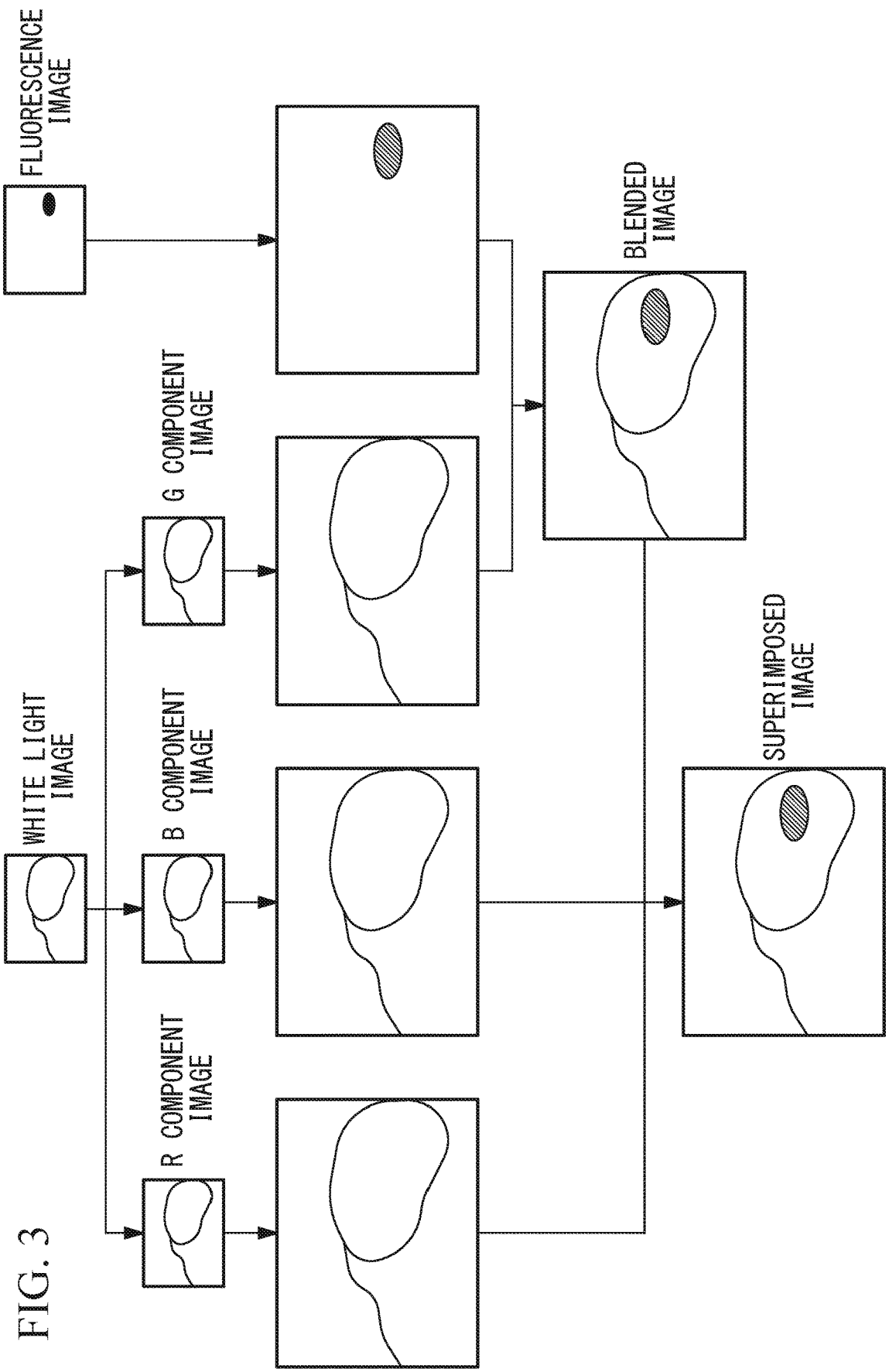
FIG. 3 is an explanatory diagram of one example of processing a white light image and a fluorescence image at the image processing unit in FIG. 2.

As illustrated in FIG. 2, the image processing unit 22 includes an enlargement/reduction unit 31, a blended image generation unit 32, and a superimposed image generation unit 33. FIG. 3 shows an example of a process in which the image processing unit 22 generates a superimposed image from a white light image and a fluorescence image. A white light image signal acquired by photographing of wideband white light, is formed of three color image signals, that is, a red (R) image signal, a green (G) image signal, and a blue (B) image signal. The data buffer 21 transmits the R, G, B image signals and the fluorescence image signal to the enlargement/reduction unit 31.

The enlargement/reduction unit 31 generates R, G, B component images from the R, G, B image signals, respectively, and generates a fluorescence image from the fluorescence image signal. The images are each composed of multiple pixels that are two-dimensionally arranged in a matrix form. Further, the enlargement/reduction unit 31 acquires, from the input unit 25, a display magnification inputted to the input unit 25, and receives information about the specifications of the display area of the display device 3 from the display device 3 connected with the image processing device 1. The specifications of the display area at least include the size (display size) and the number of pixels (resolution) thereof.

Next, the enlargement/reduction unit 31 determines a magnification on the basis of the display magnification and the size and the number of pixels of the display area of the display device 3, and enlarges or reduces the R, G, B component images and the fluorescence image at the determined magnification. Hereinafter, a magnification indicating enlargement of an image is referred to as "enlargement rate", and a magnification indicating reduction of an image is referred to as "reduction rate". For example, when the magnification representing the rate of unmagnification is 100%, a magnification higher than 100% is referred to as "enlargement rate", and a magnification lower than 100% is referred to as "reduction rate".

Reduction of an image is performed by thinning out of some pixels in the image so as to decrease the number of pixels therein, for example. Enlargement of an image is performed by addition of blank pixels to the image so as to increase the number of pixels therein, and by interpolation of the gradation values of the added blank pixels based on the gradation values of the surrounding pixels, for example. The enlargement/reduction unit 31 transmits the enlarged or reduced G component image and the enlarged or reduced fluorescence image to the blended image generation unit 32, and transmits the enlarged or reduced R component image and the enlarged or reduced B component image to the superimposed image generation unit 33.

The blended image generation unit 32 executes a blending process by using the enlarged or reduced G component image and the enlarged or reduced fluorescence image, and thereby generates a blended image in which pixels of the G component image and pixels of the fluorescence image coexist.

Figure 4:
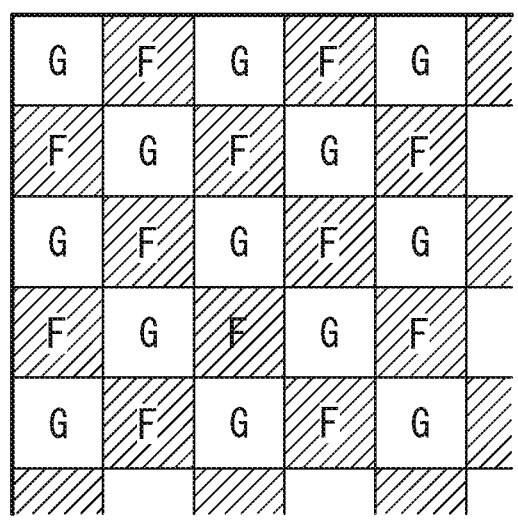
FIG. 4 is a diagram showing one example of a blending pattern which is used at a blended image generation unit in FIG. 2.

Specifically, the blended image generation unit 32 holds a blending pattern which specifies the arrangement of the pixels "G" of the G component image and the pixels "F" of the fluorescence image. For example, the blending pattern is a square lattice arrangement pattern in which the pixels "G" and "F" are arranged, in a check pattern form, alternately one by one in the row direction and the column direction, as shown in FIG. 4. The blended image generation unit 32 replaces pixels, among all the pixels of the G component image, corresponding to "F" of the blending pattern, with pixels of the fluorescence image, and thereby generates the blended image in which distribution of the pixels of the G component image and the pixels of the fluorescence image blended therein is substantially uniform over the blended image.

The pattern of "G" and "F" in the blended image can be changed as long as the distribution of "G" and "F" is substantially uniform over the blended image. For example, a blending pattern having another arrangement of "G" and "F" may be adopted. Alternatively, the blended image generation unit 32 may substantially uniformly select some pixels at random from among all the pixels of the G component image.

The superimposed image generation unit 33 uses the blended image received from the blended image generation unit 32, in place of the G component image, and performs color synthesis of the blended image and the R component image and the B component image received from the enlargement/reduction unit 31, and thereby generates a color superimposed image. The superimposed image generation unit 33 transmits the generated superimposed image to the display image buffer 23.

The display image buffer 23 temporarily holds the superimposed image received from the superimposed image generation unit 33, and outputs the superimposed image to the display device 3 via the D/A converter 29 at a fixed time interval.

Next, operations of the image processing device 1 and the endoscope system 100 configured as described above will be described.

In order to observe the biotissue A with use of the endoscope system 100, a fluorescent substance, which is accumulated in a lesion part, is preliminarily administered to the biotissue A.

First, the insertion part 5 is inserted into a human body, the distal end 5a is put so as to face the biotissue A, and white light and excitation light are alternately applied from the distal end 5a of the insertion part 5 to the biotissue A by the light source unit 4 being operated.

When the white light is applied to the biotissue A, the white light having been reflected by a surface of the biotissue A is collected by the objective lens 14. The white light collected by the objective lens 14 passes through the notch filter 16, enters the image pickup element 15, and is obtained as a white light image signal by the image pickup element 15. On the other hand, when the excitation light is applied to the biotissue A, the fluorescent substance included in the lesion part is excited by the excitation light so that fluorescence is generated. The fluorescence and a part of the excitation light are collected by the objective lens 14. Of the fluorescence and the excitation light collected by the objective lens 14, only the fluorescence passes through the notch filter 16, enters the image pickup element 15, and is acquired as a fluorescence image signal by the image pickup element 15.

The white light image signal and the fluorescence image signal alternately acquired by the image pickup element 15, as described above, are transmitted to the image processing device 1.

In the image processing device 1, the white light image signal and the fluorescence image signal are inputted to the data buffer 21 via the amplifier 26, the AGC 27, and the A/D converter 28. One pair of the white light image signal and the fluorescence image signal is inputted from the data buffer 21 to the image processing unit 22.

Figure 5:
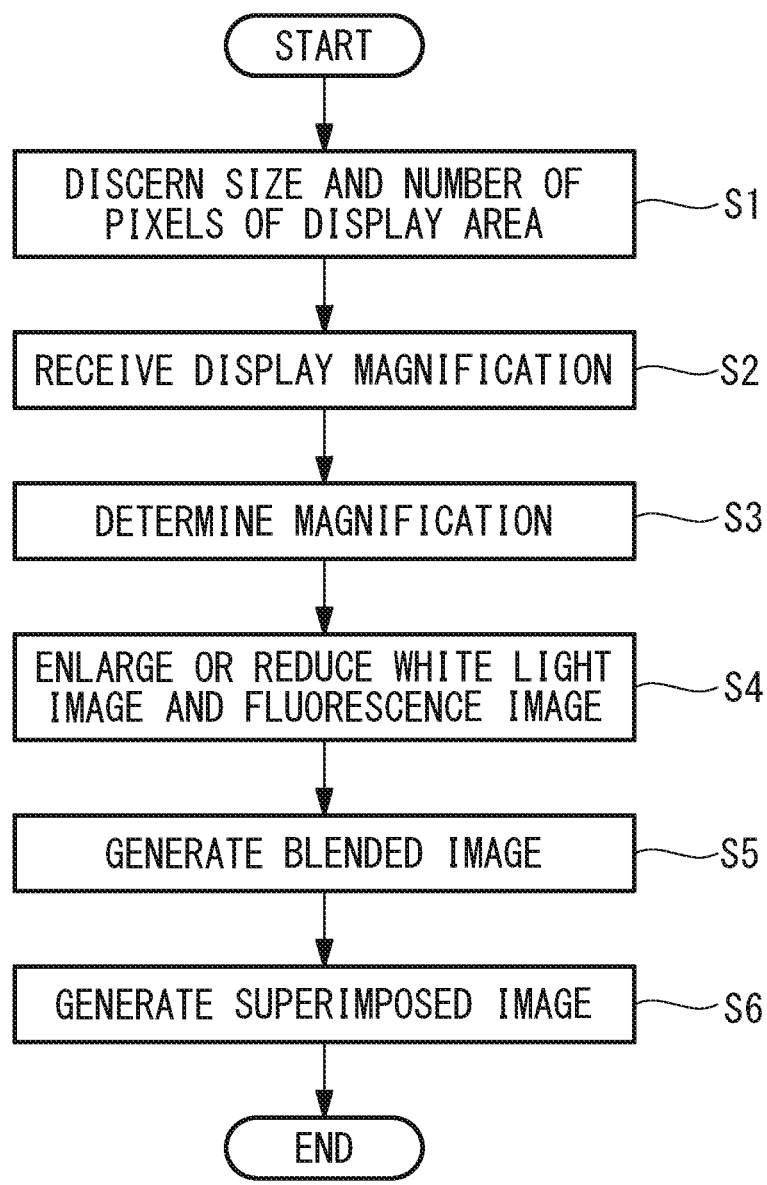
FIG. 5 is a flowchart showing operation of the endoscope image processing device in FIG. 1.

In the image processing unit 22, the specifications of the display area of the display device 3 and the display magnification inputted to the input unit 25 by the user are discerned by the enlargement/reduction unit 31 (steps S1, S2), a magnification is determined on the basis of the size of the display area, the number of the pixels in the display area, and the display magnification (step S3), as shown in FIG. 5. Next, at the enlargement/reduction unit 31, the R, G, B component images constituting the white light image, and the fluorescence image are enlarged or reduced at the determined magnification (step S4). The enlarged or reduced G component image and the enlarged or reduced fluorescence image are transmitted to the blended image generation unit 32. The enlarged or reduced R image signal and the enlarged or reduced B image signal are transmitted to the superimposed image generation unit 33.

Next, at the blended image generation unit 32, some pixels of the G component image are replaced with pixels of the fluorescence image so that a blended image in which distribution of pixels of the G component image and pixels of the fluorescence image blended therein is substantially uniform over the blended image, is generated (step S5). The blended image includes both the image of the biotissue A in the G component image and the image of the fluorescence in the fluorescence image. The generated blended image is subjected to color synthesis with the R component image and the B component image at the superimposed image generation unit 33 so that a superimposed image is generated (step S6). The generated superimposed image is sequentially transmitted, at a prescribed time interval, from the display image buffer 23 to the display device 3 via the D/A converter 29. Consequently, the superimposed image is displayed, on the display area of the display device 3, as a live image at the display magnification inputted to the input unit 25 by the user.

In this case, according to the present embodiment, the blended image is formed by blending pixels of the G component image and pixels of the fluorescence image such that the pixels coexist with the distribution thereof substantially uniform over the blended image. Irrespective of the gradation value, the fluorescence image is entirely, and substantially uniformly synthesized into the blended image. Therefore, among fluorescence regions, not only a fluorescence region having a sufficiently high gradation value but also a fluorescence region having a relatively low gradation value is synthesized into the blended image. This provides an advantageous effect that a superimposed image in which all the fluorescence regions to be noted by the observer are displayed, can be generated.

In addition, the gradation values of the pixels of the blended image are the gradation values of pixels of the G color component image themselves or the gradation values of pixels of the fluorescence image themselves. In the superimposed image formed by color synthesis using this blended image, a color tone substantially identical to the color tone of the white light image can be reproduced. Moreover, the information about the structure of the biotissue A in the white light image is not buried in the gradation value of the fluorescence image so that the clear structure of the biotissue A in the white light image can be maintained in the superimposed image. Furthermore, even when the SN ratio of the fluorescence image is low and the fluorescence image includes noise, the noise is reduced in the blended image as a result of blending of pixels of the fluorescence image and pixels of the G component image including no noise. This provides an advantageous effect that the superimposed image having little noise can be obtained.

In addition, the superimposed image includes a mosaic pattern based on the alternate arrangement of pixels of the G component image and pixels of the fluorescence image in the blended image. If the enlargement process is performed not prior to generation of the blended image, but after the generation, the mosaic pattern in the blended image is enlarged. Accordingly, in the superimposed image enlarged at a high magnification, the mosaic pattern is enlarged to such a size as to be visually recognizable to the user. As a result, the enlarged superimposed image displayed on the display device 3 becomes unnatural, and further, the mosaic pattern infers observation of the form of the biotissue A or the fluorescence. In contrast, according to the present embodiment, the blended image is generated from the G component image and the fluorescence image that have been already enlarged, and thus, the mosaic pattern is not enlarged, and the size thereof is kept so small that the user cannot visually recognize the mosaic pattern. Accordingly, when the display magnification is increased such that the enlarged superimposed image is observed on the display area, a natural superimposed image can be provided.

Also, when the reduction process is performed not prior to generation of the blended image but after the generation, the noise of a moire, a striped pattern, or the like, based on the mosaic pattern may occur. According to the present embodiment, the blending process is performed after the reduction process, whereby occurrence of noise can be prevented, and the superimposed image having no noise can be displayed at a low magnification.

In the present embodiment, the image processing device 1 and the display device 3 are separated from each other. Alternatively, the image processing device 1 and the display device 3 may be integrated with each other. That is, the image processing device 1 may have a display area, and may have a display function of displaying a superimposed image in the display area.

This configuration is advantageous because, when the final display size of the superimposed image is adjusted at the display side, information about the display size is transmitted to the enlargement/reduction unit 31 within the same device.

In addition, in the present embodiment, the image processing unit 22 and the input unit 25 which bear the function of generating the superimposed image may be provided in a device different from a device provided with other components 21, 23, 24, 26, 27, 28, 29. In this case, the image processing device having the image processing unit 22 and the input unit 25 generates the superimposed image by using the white light image signal and the fluorescence image signal received from the other device.

Second Embodiment

Next, an endoscope image processing device according to a second embodiment of the present invention and an endoscope system provided therewith will be described with reference to FIGS. 6 to 8.

In the present embodiment, components different from those of the first embodiment will be mainly described. Components identical to those of the first embodiment are denoted by the same reference numerals, and an explanation thereof will be omitted.

The endoscope system according to the present embodiment includes the endoscope device 2, the endoscope image processing device (hereinafter, simply referred to as "image processing device") according to the present embodiment, which is connected with the endoscope device 2, and the display device 3 connected with the image processing device.

The image processing device according to the present embodiment includes the data buffer 21, an image processing unit 221, the display image buffer 23, the timing control unit 24, and the input unit 25.

Figure 6:
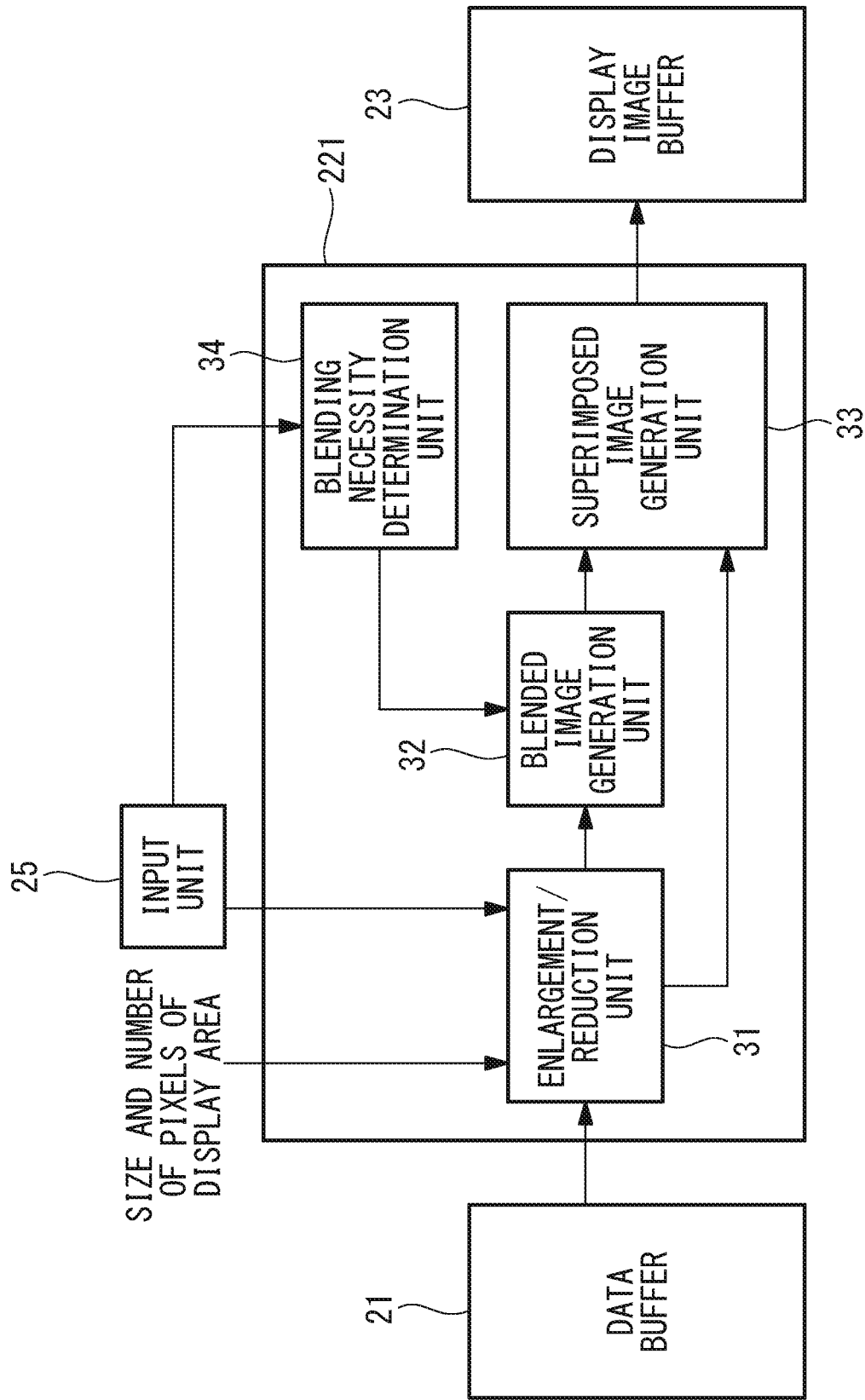
FIG. 6 is a configuration diagram of an image processing unit of an endoscope image processing device according to a second embodiment of the present invention.

As illustrated in FIG. 6, the image processing unit 221 includes the enlargement/reduction unit 31, the blended image generation unit 32, and the superimposed image generation unit 33, and further includes a blending necessity determination unit 34 that performs, on the basis of a display magnification inputted to the input unit 25, switching between execution and non-execution of the blending process at the blended image generation unit 32.

The blending necessity determination unit 34 acquires the display magnification from the input unit 25. When the display magnification is an enlargement rate equal to or higher than a predetermined threshold, the blending necessity determination unit 34 sets an "OFF" state in which the blending process is not executed. In contrast, when the display magnification is a reduction rate, the rate of unmagnification, or an enlargement rate lower than the predetermined threshold, the blending necessity determination unit 34 sets an "ON" state in which the blending process is executed. That is, when the superimposed image is enlarged and displayed at a high magnification on the display area, the "OFF" of the blending process is set. Otherwise, the "ON" of the blending process is set.

When the "ON" is set, the blended image generation unit 32 executes the blending process to generate the blended image. In contrast, when the "OFF" is set, the blended image generation unit 32 does not execute the blending process but directly transmits, to the superimposed image generation unit 33, the enlarged G component image received from the enlargement/reduction unit 31.

Figure 7:
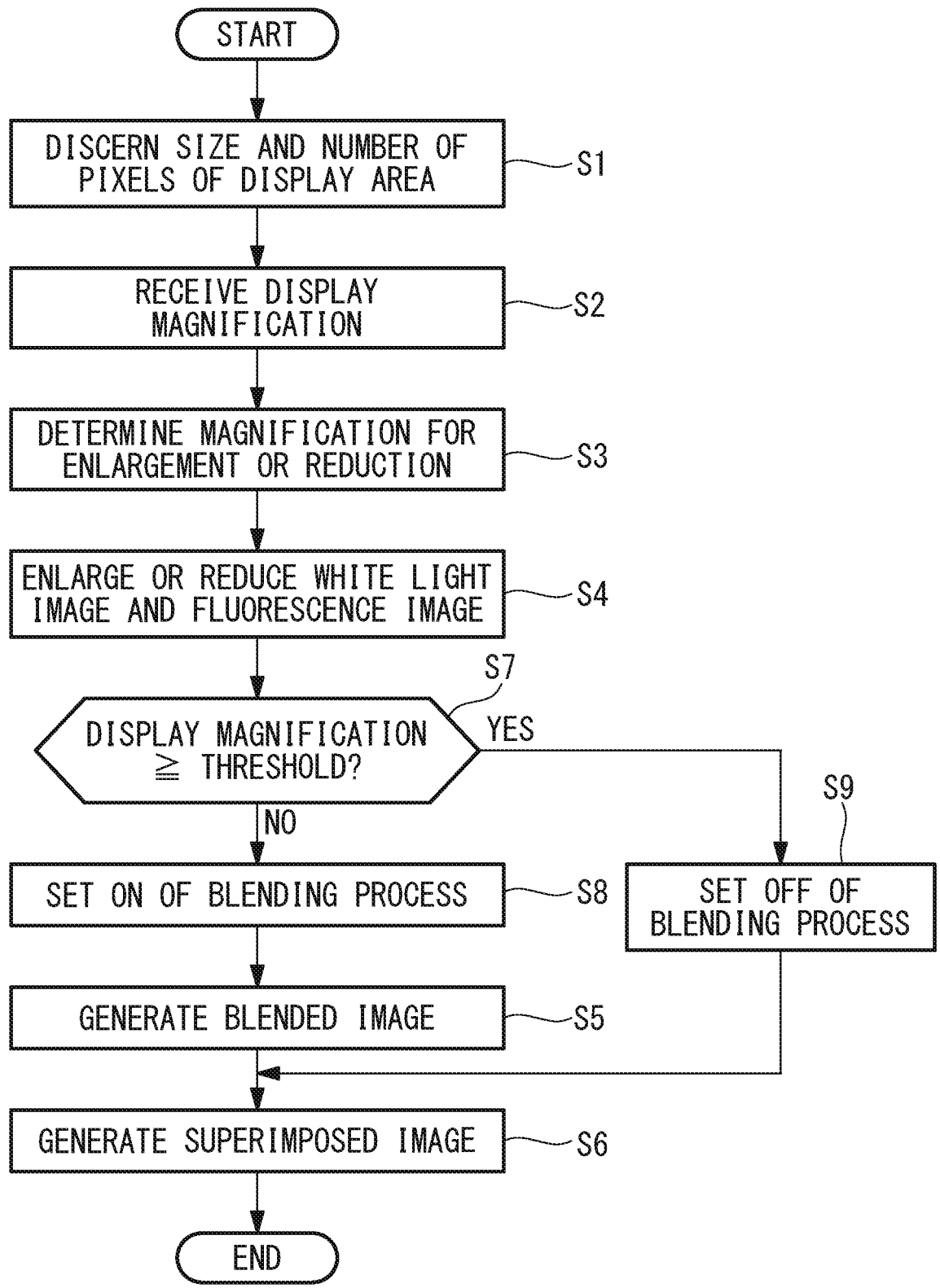
FIG. 7 is a flowchart showing operation of the endoscope image processing device including the image processing unit in FIG. 6.
Figure 8:
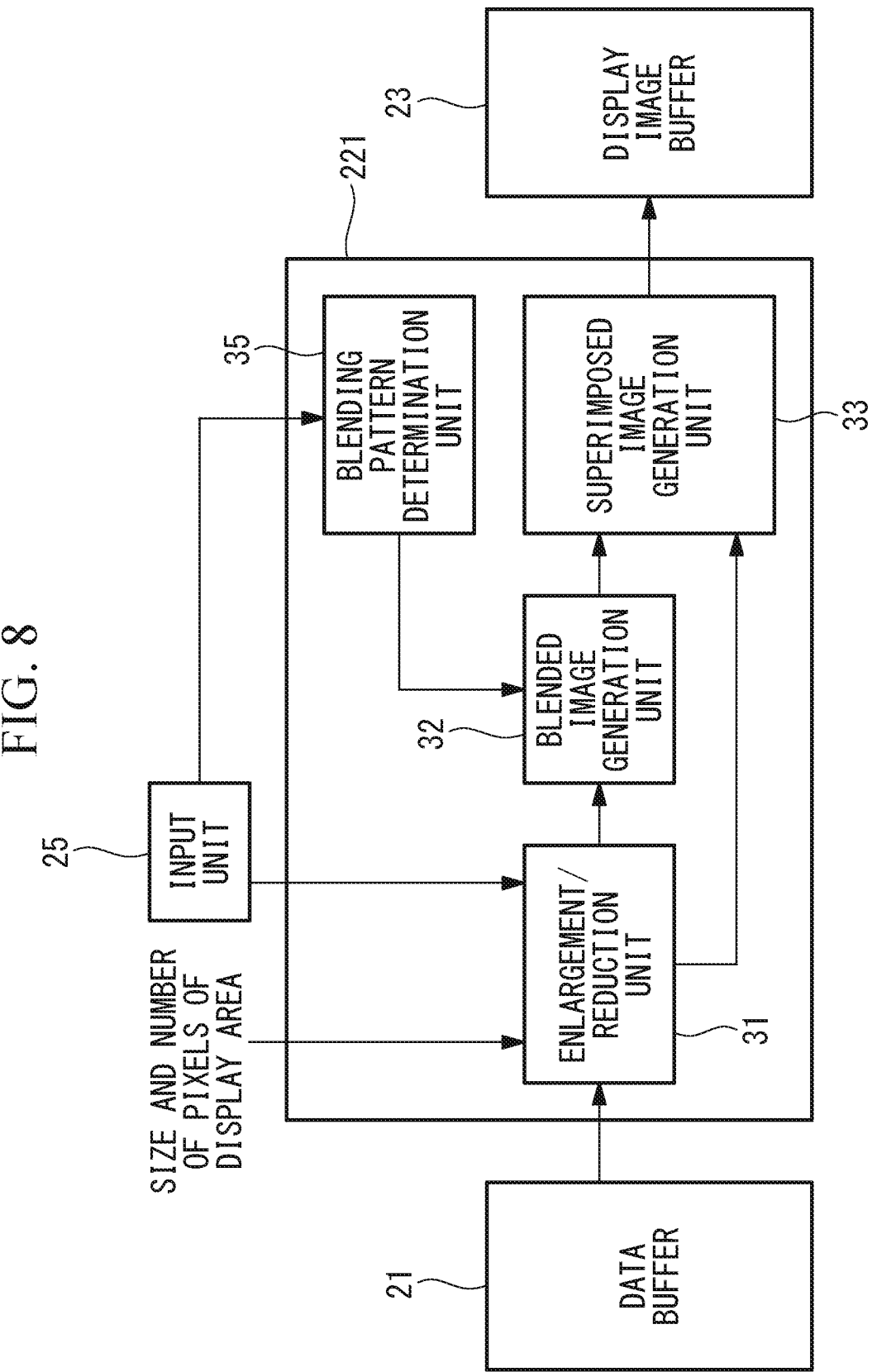
FIG. 8 is a configuration diagram of a modification of the image processing unit in FIG. 6.

According to the present embodiment, when the display magnification inputted to the input unit 25 by the user is lower than the threshold (NO at step S7), the "ON" of the blending process is set (step S8), the blended image is generated from the enlarged G component image and the enlarged fluorescence image (step S5), and the superimposed image is generated with use of the generated blended image (step S6), as shown in FIG. 7. On the other hand, when the display magnification inputted to the input unit 25 by the user is equal to or higher than the threshold (YES at step S7), the "OFF" of the blending process is set (step S9), and the enlarged G component image is directly used in color synthesis, whereby an image is generated (step S6). That is, in this case, at step S6, a white light image is generated rather than the superimposed image.

When the observer desires to observe a region of interest such as a lesion part in detail, the superimposed image is enlarged and displayed at a high magnification on the display area. At this time, the blending process is switched to "OFF" so that the image in which the form of the biotissue A is more definite is displayed in the display area. Consequently, display suitable for the observation scene can be performed, and the amount of image processing can be reduced.

The other operations and effects of the present embodiment are identical to those of the first embodiment. Thus, an explanation thereof is omitted.

In the present embodiment, when an image enlarged at a high magnification is displayed, the blending process is switched to "OFF", whereby the definition of the biotissue A in the image is enhanced. Alternatively, the ratio of the number of pixels "F" of the fluorescence image in the blended image which is included in the superimposed image may be lowered. Specifically, a blending pattern determination unit 35 that determines a blending pattern to be used by the blended image generation unit 32 according to the magnification, may be further provided in the image processing unit 221, as illustrated in FIG. 8.

Figure 9:
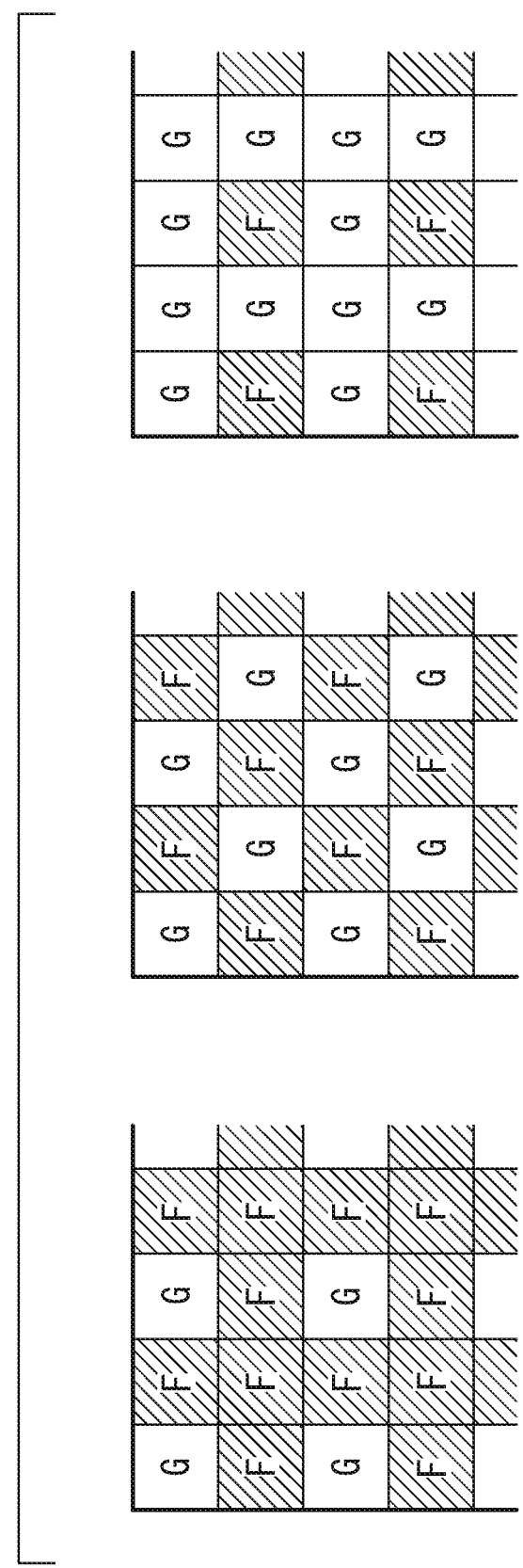
FIG. 9 is a diagram showing a plurality of blending patterns which a blending pattern determination unit in FIG. 8 has.

The blending pattern determination unit 35 acquires, from the enlargement/reduction unit 31, the magnification determined by the enlargement/reduction unit 31. When the magnification is an enlargement rate, the enlargement/reduction unit 31 determines a blending pattern such that, when the enlargement rate is higher, the ratio of the number of "F" is smaller. For example, the blending pattern determination unit 35 stores a plurality of blending patterns having the different ratios of the number of "F", as shown in FIG. 9. Further, the blending pattern determination unit 35 stores the correspondence between the enlargement rate and the ratio of the number of "F". The blending pattern determination unit 35 selects a blending pattern having the ratio of the number of "F" corresponding to the enlargement rate, and sets the selected blending pattern on the blended image generation unit 32.

As a result of this, in the case where the superimposed image is enlarged and displayed at a high magnification on the display area, the blended image in which the blending ratio of the fluorescence image is low and the blending ratio of the white light image is high is generated. Thus, the superimposed image in which the form of the biotissue A is more definite is generated. In any other case, the superimposed image in which the fluorescent regions of the fluorescence image are clear is generated. As described above, a superimposed image suitable for an observation scene can be provided to a user.

The image processing unit 221 may be provided with both the blending necessity determination unit 34 and the blending pattern determination unit 35, or may be provided with only either one of the blending necessity determination unit 34 and the blending pattern determination unit 35. In the case where both the blending necessity determination unit 34 and the blending pattern determination unit 35 are provided, the blending pattern determination unit 35 is operated only when the "ON" is set by the blending necessity determination unit 34.

Third Embodiment

Next, an endoscope image processing device according to a third embodiment of the present invention and an endoscope system provided therewith will be described with reference to FIGS. 10 to 12C.

In the present embodiment, components different from those of the first and second embodiments will be mainly described. Components identical to those of the first and second embodiments are denoted by the same reference numerals, and an explanation thereof will be omitted.

The endoscope system according to the present embodiment includes the endoscope device 2, the endoscope image processing device (hereinafter, simply referred to as "image processing device") according to the present embodiment, which is connected with the endoscope device 2, and the display device 3 connected with the image processing device.

The image processing device according to the present embodiment includes the data buffer 21, an image processing unit 222, the display image buffer 23, the timing control unit 24, and the input unit 25.

Figure 10:
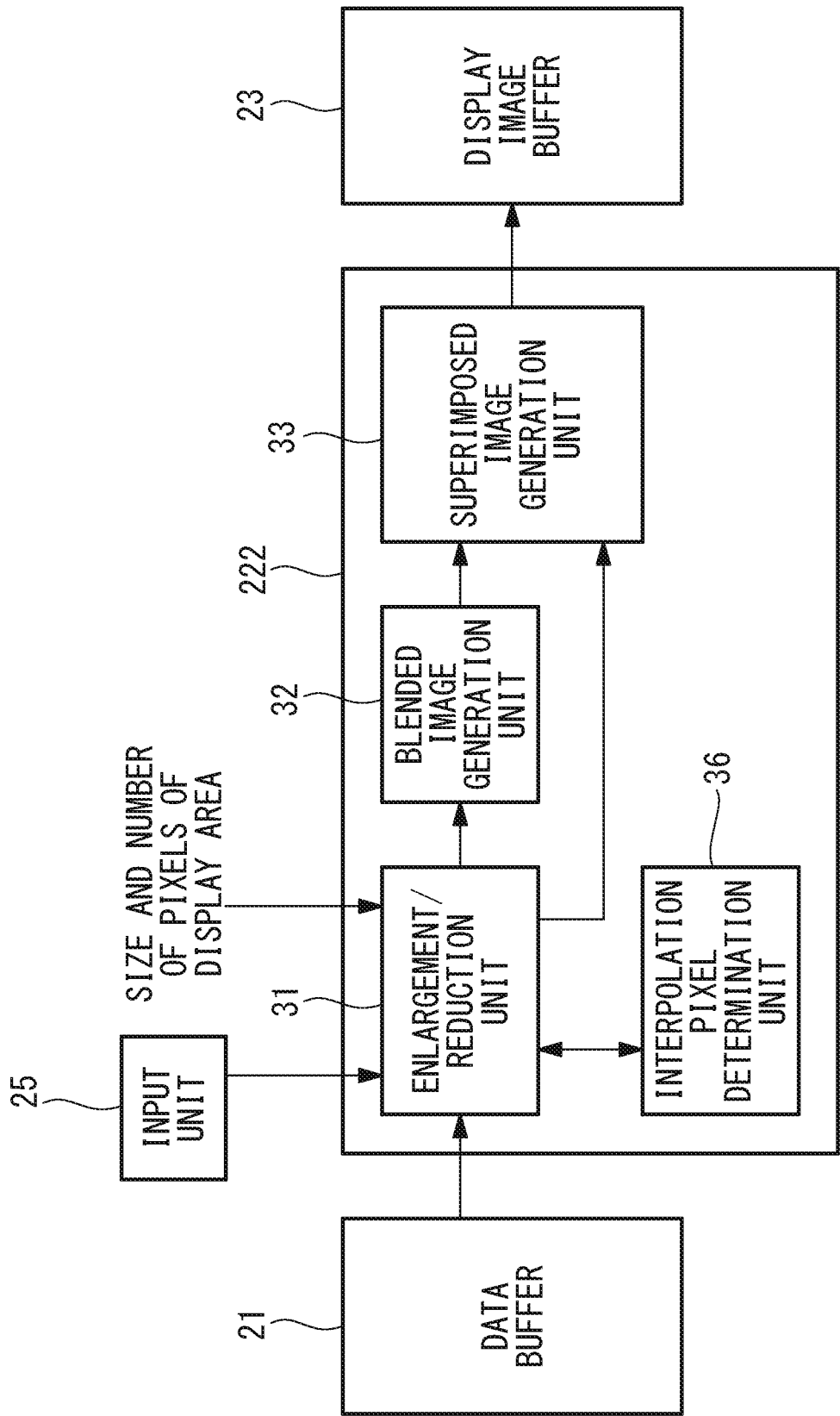
FIG. 10 is a configuration diagram of an image processing unit of an endoscope image processing device according to a third embodiment of the present invention.

As illustrated in FIG. 10, the image processing unit 222 includes not only the enlargement/reduction unit 31, the blended image generation unit 32, and the superimposed image generation unit 33, but also an interpolation pixel determination unit 36 that determines a blank pixel the gradation value of which is to be interpolated during the enlargement process of the G component image and the fluorescence image.

FIGS. 11A to 12C show a process of, when the enlargement rate is 2×, generating the superimposed image with use of the blending pattern shown in FIG. 4. FIG. 11B shows an image obtained by enlarging the G component image in FIG. 11A. FIG. 12B shows an image obtained by enlarging the fluorescence image in FIG. 12A. FIGS. 11C and 12C each show an example in which each pixel value is interpolated by a bilinear method using the gradation values of four surrounding pixels. However, another interpolation method may be used.

The interpolation pixel determination unit 36 stores an enlargement rate and address information indicating the positions of pixels the gradation values of which are to be interpolated, in association with each other. The address information is information indicating the positions of, among blank pixels added to the G component image and the fluorescence image, pixels (pixels surrounded by broken lines in FIGS. 11B and 12B) constituting the blended image. That is, the address information for the G component image is information indicating the positions of, among the blank pixels added to the G component image, pixels other than the pixels to be replaced with pixels "F" of the fluorescence image. Address information for the fluorescence image is information indicating the positions of, among blank pixels added to the fluorescence image, pixels (pixels corresponding to pixels "F" of the blending pattern) to be used for replacement of the pixels in the G component image.

The interpolation pixel determination unit 36 acquires, from the enlargement/reduction unit 31, the magnification determined by the enlargement/reduction unit 31. When the magnification is an enlargement rate, the interpolation pixel determination unit 36 selects the address information corresponding to the enlargement rate, and transmits the selected address information to the enlargement/reduction unit 31.

The enlargement/reduction unit 31 enlarges the G component image by adding blank pixels to the G component image, as shown in FIGS. 11A and 11B. Similarly, the enlargement/reduction unit 31 enlarges the fluorescence image by adding blank pixels to the fluorescence image, as shown in FIGS. 12A and 12B. Next, the enlargement/reduction unit 31 interpolates the gradation values of, among the blank pixels added to the G component image, only blank pixels at the positions indicated by the address information, and does not perform interpolation on the other blank pixels, as shown in FIG. 11C. Similarly, the enlargement/reduction unit 31 interpolates the gradation values of, among the blank pixels added to the fluorescence image, only blank pixels at the positions indicated by the address information, and does not execute interpolation on the other blank pixels, as shown in FIG. 12C. Consequently, the enlarged G component image and the enlarged fluorescence image transmitted from the enlargement/reduction unit 31 to the blended image generation unit 32 can include blank pixels having no gradation value, as shown in FIGS. 11C and 12C.

The address information varies, depending on the blending pattern besides the magnification rate. Therefore, in a case where a plurality of blending patterns can be used at the enlargement/reduction unit 31, address information corresponding to each combination of an enlargement rate and a blending pattern is stored in the interpolation pixel determination unit 36 so that the address information selected on the basis of a combination of an enlargement rate and a blending pattern is used for the interpolation process at the enlargement/reduction unit 31.

When the gradation values of all the added blank pixels are interpolated in the enlargement process of the white light image and the fluorescence image, the amount of image processing and the temporal storage capacity in the image processing device are increased. According to the present embodiment, the gradation values of only blank pixels required for generation of the blended image are interpolated, whereby the amount of processing and the storage capacity can be reduced.

In addition, positions at which blank pixels are added to the G component image are made different from positions at which blank pixels are added to the fluorescence image such that the positions of the original pixels G11, G12, . . . , G33 of the G component image to which the blank pixels have been added are different from the positions of the original pixels F11, F12, . . . , F23 of the fluorescence image to which the blank pixels have been added, as shown in FIGS. 11B and 12B. Accordingly, the number of blank pixels the gradation values of which is to be interpolated can be further reduced.

The other operations and effects of the present embodiment are identical to those of the first embodiment. Thus, an explanation thereof is omitted.

In each of the first to third embodiments, the enlargement/reduction process has been described as image processing that is executed prior to the blending process. However, an advantageous effect can be obtained also in a case where image processing other than the enlargement/reduction process is executed prior to the blending process. Therefore, instead of the enlargement/reduction process or in addition to the enlargement/reduction process, other image processing may be executed prior to the blending process.

For example, when various emphasis processes such as a structure emphasis process and a contour emphasis process are performed after the blending process, appropriate emphasis of an image of the biotissue A in the white light image or an image of the fluorescence in the fluorescence image may fail because the emphasis processes are influenced by the mosaic pattern. When such emphasis processes are executed prior to the blending process, the emphasis processes appropriately succeed.

In each of the first to third embodiments, the white light and the excitation light are alternately applied to the biotissue A, and the white light image signal and the fluorescence image signal are alternately acquired with use of the single image pickup element 15. Alternatively, a configuration may be adopted in which the white light and the excitation light may be simultaneously applied to the biotissue A, and the white light image signal and the fluorescence image signal may be simultaneously acquired with use of two image pickup elements 15.

In each of the first to third embodiments, the fluorescence image is blended to the G component image such that the fluorescent regions are displayed in green in the superimposed image. However, the fluorescence image may be blended to the R component image or to the B component image.

In each of the first to third embodiments, the excitation light which excites a fluorescent substance and the fluorescence image have been described as one example of the narrow-band light and one example of the narrow-band light image, respectively. However, the type of the narrow-band light and the type of the narrow-band light image are not limited thereto. For example, an infrared light image may be acquired with use of infrared light, or an NBI image may be acquired with use of blue narrow-band light and green narrow-band light.

The image processing device 1 having been described in the first to third embodiments, is implemented by a computer provided with a central processing unit (CPU) and a storage, for example. Specifically, an image processing program for causing the CPU to execute the processes to be performed by the image processing unit 22, 221, 222, is stored in the storage, and the processes to be performed by the components 31, 32, 33, 34, 35, 36 are implemented by the CPU operating in accordance with the image processing program.

The above-described embodiment also leads to the following invention.

One aspect of the present invention is an endoscope image processing device processing a color normal light image of a subject illuminated with wide-band visible light and a narrow-band light image of the subject illuminated with a narrow-band light, the image processing device including: an enlargement/reduction unit that enlarges or reduces multiple color component images constituting the normal light image, and the narrow-band light image; a blended image generation unit that generates a blended image by synthesizing one of the color component images enlarged or reduced by the enlargement/reduction unit and the narrow-band light image enlarged or reduced by the enlargement/reduction unit; and a superimposed image generation unit that generates a color superimposed image by synthesizing the blended image generated by the blended image generation unit and the other color component images enlarged or reduced by the enlargement/reduction unit, wherein the blended image generation unit generates the blended image by selecting some of pixels of the one enlarged or reduced color component image, and replacing the selected pixels with corresponding pixels of the enlarged or reduced narrow-band light image, and replaces some of pixels of the one enlarged or reduced color component image with the pixels of the enlarged or reduced narrow-band light image such that distribution of pixels of the one enlarged or reduced color component image and pixels of the enlarged or reduced narrow-band light image is substantially uniform over the blended image.

According to the present aspect, after the normal light image and the narrow-band light image are enlarged or reduced, the color normal light image is divided into the one color component image and the other color component images, and the one color component image and the narrow-band light image are synthesized, whereby the blended image is generated. The generated blended image and the other color component images are subjected to color synthesis by the superimposed image generation unit. Consequently, the narrow-band light image is superimposed on the normal light image so that the enlarged or reduced superimposed image can be obtained.

In this case, the narrow-band light image is entirely synthesized with the blended image in a substantially uniform manner, without undergoing a process for extracting only a partial region therefrom. Therefore, all the regions of interest each having a gradation value in the narrow-band light image can be displayed in the superimposed image.

In addition, since the pixels of the one color component image and the pixels of the narrow-band light image coexist directly in the blended image, a gradation value change in the blended image with respect to the one color component image is reduced, and noise included in the narrow-band light image is reduced in the blended image. Moreover, information about the structure of the subject in the normal light image is not buried in the gradation value of the narrow-band light image. Consequently, the superimposed image in which a color tone change is small and less noise is included, compared to those of the normal light image, and the structure of the subject is clear, can be generated.

Furthermore, the superimposed image including the blended image includes a mosaic pattern which derives from arrangement of the pixels of the normal light image and the pixels derived from the narrow-band light image in the blended image. If enlargement or reduction is performed after the blended image is generated, an artifact caused by the mosaic pattern included in the blended image may be generated. In contrast, when the blended image is generated from the normal light image and the narrow-band light image that have been already enlarged or reduced, occurrence of an artifact is prevented during the enlargement/reduction process. Thus, a superimposed image that is natural can be provided.

In the above aspect, the enlargement/reduction unit may acquire a display size of the superimposed image from a display device displaying the superimposed image, and enlarge or reduce the normal light image and the narrow-band light image at a magnification corresponding to the acquired display size.

Accordingly, the display size of the superimposed image on the display device is automatically discerned so that the superimposed image can be enlarged or reduced to a size suitable for display.

In the above aspect, an input unit to which a display magnification for the superimposed image is inputted by a user may be provided, and the enlargement/reduction unit may enlarge or reduce the normal light image and the narrow-band light image at a magnification corresponding to the display magnification inputted to the input unit.

Accordingly, the superimposed image enlarged or reduced according to a display magnification desired by the user can be provided.

In the above aspect, a blending necessity determination unit that determines, based on the magnification, whether or not to cause the blended image generation unit to generate the blended image, may be provided.

When generation of the blended image is halted, color synthesis of the one enlarged or reduced color component image rather than the blended image, with the other enlarged or reduced color component images is performed at the superimposed image generation unit. Thus, the enlarged or reduced normal light image is generated. At a certain display magnification, the normal light image becomes more suitable for observation than the superimposed image including the blended image. Therefore, for such a display magnification, generation of the blended image is halted, and the enlarged or reduced normal light image rather than the superimposed image is generated so that an image more suitable for an observation scene can be provided.

In the above aspect, a blending pattern determination unit that sets, on the blended image generation unit, a blending pattern which specifies arrangement of pixels of the one enlarged or reduced color component image and pixels of the enlarged or reduced narrow-band light image in the blended image, and that determines the blending pattern according to the magnification such that when the magnification is higher, the ratio of the number of pixels of the enlarged or reduced narrow-band light image is lower, may be provided, and the blended image generation unit may generate the blended image in accordance with the blending pattern set by the blending pattern determination unit.

Accordingly, when the magnification is high, the superimposed image in which the blending ratio of the normal light image is high and the form of the subject is more definite is provided. In contrast, when the magnification is low, the superimposed image in which the blending ratio of the narrow-band light image is high and a region of interest such as a lesion part, which is to be observed with narrow-band light, is more enhanced, is provided. In this way, a superimposed image suitable for various observation scenes can be provided.

In the above aspect, the enlargement/reduction unit may enlarge the normal light image and the narrow-band light image by adding pixels to the normal light image and the narrow-band light image so as to increase the number of pixels therein, and interpolating gradation values of at least some of the added pixels, and an interpolation pixel determination unit that determines, according to the magnification, a pixel a gradation value of which is to be interpolated, such that at least pixel values of pixels to constitute the blended image are interpolated, may be provided.

Some of the pixels added to the one color component image and the narrow-band light image are not used in the blended image. Therefore, when a pixel the pixel value of which is to be interpolated is selected during enlargement of the one color component image and the narrow-band light image, the processing amount and the storage capacity for the enlarged image can be reduced. In particular, the interpolation pixel determination unit determines only the pixels to constitute the blended image to be pixels gradation values of which are to be interpolated, so that the processing amount and the storage capacity can be minimized.

REFERENCE SIGNS LIST

100 endoscope system
1 endoscope image processing device 2 endoscope device
3 display device
4 light source unit
5 insertion part
6 white light source
7 excitation light source
8 beam splitter
9 lens
10 lighting unit
11 image pickup unit
12 light guide fiber
13 lighting optical system
14 objective lens
15 image pickup element
16 notch filter
21 data buffer
22, 221, 222 image processing unit
23 display image buffer
24 timing control unit
25 input unit
26 amplifier
27 AGC
28 A/D converter
29 D/A converter
31 enlargement/reduction unit
32 blended image generation unit
33 superimposed image generation unit
34 blending necessity determination unit
35 blending pattern determination unit
36 interpolation pixel determination unit

The invention claimed is:

1. An endoscope image processing device processing a color normal light image of a subject illuminated with wide-band visible light and a narrow-band light image of the subject illuminated with a narrow-band light, the image processing device comprising:
a processor comprising hardware programmed to:
enlarge or reduce multiple color component images constituting the normal light image, and the narrow-band light image;
generate a blended image by synthesizing one of the enlarged or reduced color component images and the enlarged or reduced narrow-band light image; and
generate a color superimposed image by synthesizing the blended image and the other enlarged or reduced color component images, wherein
the processor is programmed to generate the blended image by selecting some of pixels of the one enlarged or reduced color component image, and replacing the selected pixels with corresponding pixels of the enlarged or reduced narrow-band light image, and replace some of pixels of the one enlarged or reduced color component image with pixels of the enlarged or reduced narrow-band light image such that distribution of pixels of the one enlarged or reduced color component image and pixels of the enlarged or reduced narrow-band light image is substantially uniform over the blended image.

2. The endoscope image processing device according to claim 1, wherein
the processor is programmed to acquire a display size of the superimposed image from a display displaying the superimposed image, and enlarge or reduce the normal light image and the narrow-band light image at a magnification corresponding to the acquired display size.

3. The endoscope image processing device according to claim 1, wherein
the processor is programmed to enlarge or reduce the normal light image and the narrow-band light image at a magnification corresponding to a display magnification inputted by a user.

4. The endoscope image processing device according to claim 2, wherein
the processor is programmed to enlarge or reduce the normal light image and the narrow-band light image at a magnification corresponding to a display magnification inputted by a user.

5. The endoscope image processing device according to claim 3, wherein the processor is programmed to determine whether or not to generate the blended image based on the display magnification.

6. The endoscope image processing device according to claim 4, wherein the processor is programmed to determine whether or not to generate the blended image based on the display magnification.

7. The endoscope image processing device according to claim 2, wherein the processor is programmed to:
determine a blending pattern according to the magnification such that when the magnification is higher, the ratio of the number of pixels of the enlarged or reduced narrow-band light image is lower, the blending pattern specifying arrangement of pixels of the one enlarged or reduced color component image and pixels of the enlarged or reduced narrow-band light image in the blended image; and
generate the blended image in accordance with the determined blending pattern.

8. The endoscope image processing device according to claim 3, wherein the processor is programmed to:
determine a blending pattern according to the magnification such that when the magnification is higher, the ratio of the number of pixels of the enlarged or reduced narrow-band light image is lower, the blending pattern specifying arrangement of pixels of the one enlarged or reduced color component image and pixels of the enlarged or reduced narrow-band light image in the blended image; and
generate the blended image in accordance with the determined blending pattern.

9. The endoscope image processing device according to claim 4, wherein the processor is programmed to:
determine a blending pattern according to the magnification such that when the magnification is higher, the ratio of the number of pixels of the enlarged or reduced narrow-band light image is lower, the blending pattern specifying arrangement of pixels of the one enlarged or reduced color component image and pixels of the enlarged or reduced narrow-band light image in the blended image; and
generate the blended image in accordance with the determined blending pattern.

10. The endoscope image processing device according to claim 5, wherein the processor is programmed to:
determine a blending pattern according to the magnification such that when the magnification is higher, the ratio of the number of pixels of the enlarged or reduced narrow-band light image is lower, the blending pattern specifying arrangement of pixels of the one enlarged or reduced color component image and pixels of the enlarged or reduced narrow-band light image in the blended image; and generate the blended image in accordance with the determined blending pattern.

11. The endoscope image processing device according to claim 6, wherein the processor is programmed to:
   determine a blending pattern according to the magnification such that when the magnification is higher, the ratio of the number of pixels of the enlarged or reduced narrow-band light image is lower, the blending pattern specifying arrangement of pixels of the one enlarged or reduced color component image and pixels of the enlarged or reduced narrow-band light image in the blended image; and
   generate the blended image in accordance with the determined blending pattern.

12. The endoscope image processing device according to claim 2, wherein the processor is programmed to:
   enlarge the normal light image and the narrow-band light image by adding pixels to the normal light image and the narrow-band light image so as to increase the number of pixels therein, and interpolating gradation values of at least some of the added pixels; and
   determine a pixel a gradation value of which is to be interpolated according to the magnification, such that at least pixel values of pixels to constitute the blended image are interpolated.

13. The endoscope image processing device according to claim 12, wherein the processor is programmed to determine only the pixels to constitute the blended image to be pixels gradation values of which are to be interpolated.

* * * * *